United States Patent
Mansker et al.

(10) Patent No.: US 10,049,418 B2
(45) Date of Patent: Aug. 14, 2018

(54) RESOURCE MANAGEMENT IN A MULTI-MODALITY MEDICAL SYSTEM

(71) Applicant: Volcano Corporation, San Diego, CA (US)

(72) Inventors: Richard E. Mansker, Sacramento, CA (US); Bill Clark, Davis, CA (US); Rex Kerr, Folsom, CA (US); Jason Spencer, Rocklin, CA (US)

(73) Assignee: VOLCANO CORPORATION, San Diego, CA (US)

( * ) Notice: Subject to any disclaimer, the term of this patent is extended or adjusted under 35 U.S.C. 154(b) by 282 days.

(21) Appl. No.: 14/103,555

(22) Filed: Dec. 11, 2013

(65) Prior Publication Data

US 2014/0180702 A1    Jun. 26, 2014

Related U.S. Application Data

(60) Provisional application No. 61/739,833, filed on Dec. 20, 2012.

(51) Int. Cl.
*G06F 19/00* (2018.01)
*G16H 40/60* (2018.01)
*G06Q 50/22* (2018.01)

(52) U.S. Cl.
CPC .............. *G06Q 50/22* (2013.01); *G06F 19/00* (2013.01); *G16H 40/60* (2018.01)

(58) Field of Classification Search
CPC .............. G06F 21/604; G06F 19/3406; G06F 19/3418; G06F 19/3412; G06F 19/00; G16H 40/60

(Continued)

(56) References Cited

U.S. PATENT DOCUMENTS

| 2002/0107826 A1* | 8/2002 | Ramachandran | G06N 5/043 706/49 |
| 2003/0088290 A1* | 5/2003 | Spinelli | A61N 1/37282 607/30 |

(Continued)

FOREIGN PATENT DOCUMENTS

| KR | 10-2002-0024895 | 4/2002 | |
| WO | WO-2013049461 A2 * | 4/2013 | H04L 63/10 |

OTHER PUBLICATIONS

Rasmussen, Kasper B., "Proximity-based Access Control for Implantable Medical Devices," CCS '09, Nov. 9-13, 2009 (Year: 2009).*

(Continued)

*Primary Examiner* — Jonathan Ng
*Assistant Examiner* — John P Go

(57) ABSTRACT

Generally, the present disclosure is directed to managing shared resources in a multi-modality medical system. A multi-modality medical system acquires, stores, processes, and displays data associated with a plurality of different medical modalities. Although different, independent modules within the medical system handle different modality workflows, such modules rely on common resources in the system. The method and systems described herein coordinate usage of the common resources, such as a display viewport, among the independent modality modules. For example, a token-based, locking scheme is utilized to exclusively assign a shared resource to a single modality component. This locking scheme prevents, for example, resource deadlocks from occurring during a patient procedure, thus enhancing patient safety. This scheme also ensures, for example, that one diagnostic step in a patient procedure is completed before a second diagnostic step is started, and that all workflow operations halt in the event of an error.

19 Claims, 9 Drawing Sheets

(58) Field of Classification Search
USPC .................................................. 705/2, 3, 4
See application file for complete search history.

(56) References Cited

U.S. PATENT DOCUMENTS

| | | | |
|---|---|---|---|
| 2003/0092437 A1* | 5/2003 | Nowlin | H04W 74/04 455/420 |
| 2003/0217152 A1* | 11/2003 | Kasper, II | G06F 9/526 709/226 |
| 2005/0228255 A1* | 10/2005 | Saracen | A61B 6/0457 600/407 |
| 2006/0031099 A1* | 2/2006 | Vitello | A61M 5/14212 705/2 |
| 2006/0294022 A1* | 12/2006 | Dayan | G06F 21/105 705/65 |
| 2007/0053375 A1* | 3/2007 | Kurosawa | H04L 12/403 370/450 |
| 2007/0083687 A1 | 4/2007 | Rinaldi et al. | |
| 2007/0279187 A1* | 12/2007 | Hekmatpour | G06Q 50/22 340/5.83 |
| 2009/0276515 A1* | 11/2009 | Thomas | H04L 67/34 709/223 |
| 2009/0300599 A1* | 12/2009 | Piotrowski | G06F 21/53 717/174 |
| 2010/0251352 A1* | 9/2010 | Zarchy | G06F 21/10 726/9 |
| 2011/0022191 A1 | 1/2011 | Amit et al. | |
| 2011/0291834 A1* | 12/2011 | Boldyrev | G06F 12/1416 340/572.1 |
| 2012/0029938 A1* | 2/2012 | Lauter | G06Q 50/22 705/3 |

OTHER PUBLICATIONS

International Search Report and Written Opinion received in corresponding Patent Cooperation Treaty Application No. PCT/US2013/074178, dated Mar. 26, 2014, 13 pages.

* cited by examiner

RESOURCE MANAGEMENT IN A MULTI-MODALITY MEDICAL SYSTEM

CROSS-REFERENCE TO RELATED APPLICATIONS

The present application claims priority to and the benefit of U.S. Provisional Patent Application No. 61/739,833, filed Dec. 20, 2012, which is hereby incorporated by reference in its entirety.

TECHNICAL FIELD

Embodiments of the present disclosure relate generally to the field of medical devices and, more particularly, to resource sharing in a multi-modality medical system.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), transesophageal echocardiography, and image-guided therapy. Each of these techniques may be better suited for different diagnostic situations. To increase the chance of successful treatment, health care facilities may have a multitude of imaging, treatment, diagnostic, and sensing modalities on hand in a catheter lab during a procedure. Recently, processing systems have been designed that collect medical data from a plurality of different imaging, treatment, diagnostic, and sensing tools and process the multi-modality medical data. Such multi-component systems often include modules that are independent but rely on common resources. And, during a multi-modality workflow some level of coordination may be needed between multiple independent modules. Lack of synchronization between modules associated with different modalities may lead to resource deadlocks and, in extreme cases, may adversely affect patient safety.

Accordingly, while the existing medical processing devices and methods have been generally adequate for their intended purposes, they have not been entirely satisfactory in all respects.

SUMMARY

The present disclosure provides devices, systems, and methods for managing the resources of a multi-modality medical diagnostic and/or treatment system in an effort to improve system efficiencies, prevent unwanted processing deadlocks, and enhance patient safety and treatment outcomes.

Generally, the present disclosure is directed to managing shared resources in a multi-modality medical system. A multi-modality medical system acquires, stores, processes, and displays data associated with a plurality of different medical modalities. Although different, independent modules within the medical system handle different modality workflows, such modules rely on common resources in the system. The method and systems described herein coordinate usage of the common resources, such as a display viewport, among the independent modality modules. For example, a token-based, locking scheme is utilized to exclusively assign a shared resource to a single modality component. This locking scheme prevents, for example, resource deadlocks from occurring during a patient procedure, thus enhancing patient safety. This scheme also ensures, for example, that one diagnostic step in a patient procedure is completed before a second diagnostic step is started, and that all workflow operations halt in the event of an error.

In one exemplary aspect, the present disclosure is directed to a method of resource management in a multi-modality medical system. The system includes initializing a case associated with a patient undergoing a multi-modality medical procedure that includes a workflow action to be performed by each of a plurality of modality components within the multi-modality medical system, and, in response to initializing the case, making a token available to the plurality of modality components, the token being representative of authorization to perform the workflow action. The method also includes receiving a first request for the token from a first modality component associated with a first medical modality, passing the token to the first modality component, possession of the token by the first modality component indicating that the first modality component is authorized to perform the workflow action, and receiving the token from the first modality component. Further, the method includes receiving a second request for the token from a second modality component associated with a second medical modality different from the first medical modality and passing the token to the second modality component, possession of the token by the second modality component indicating that the second modality component is authorized to perform the workflow action.

In another exemplary aspect, the present disclosure is directed to a method of resource management in a multi-modality medical system. The method includes initializing a case associated with a patient undergoing a multi-modality medical procedure that utilizes a shared resource within the multi-modality medical system, and, subsequent to initializing the case, receiving a first request to utilize the shared resource from a first modality component associated with a first medical modality. The method also includes locking the shared resource for exclusive use by first modality component, receiving a second request to utilize the shared resource from a second modality component associated with a second medical modality different than the first medical modality, and determining if the shared resource is locked. Further, the method includes, if the shared resource is not locked, locking the shared resource for exclusive use by second modality component and, if the shared resource is locked, notifying the second modality of the lock on the shared resource.

In yet another exemplary aspect, the present disclosure is directed to a method of error management in a multi-modality medical system. The method includes passing a token to a modality component, possession of the token by the modality component indicating that the modality component is authorized to perform a workflow action in association with a patient and the modality component performing the workflow action on the patient. The method also includes detecting, while the modality component is performing the workflow action, an error that adversely affects the safety of the patient and, in response to detecting the error, revoking the token from the modality component to stop the performance of the workflow action.

In a further exemplary aspect, the present disclosure is directed to a method of display management in a medical system. The method includes passing a token to a modality component, possession of the token by the modality component indicating that the modality component is authorized to display patient data in a viewport as it is being acquired from a patient and, in response to passing the token to the modality component, making a user-selectable item displayed in the viewport temporarily unselectable, the user-selectable item being configured to present content in the viewport that obscures the patient data in response to a user selection. The method also includes displaying, while the modality component holds the token, the patient data in the viewport as it is being acquired from the patient, receiving the token from the modality component, and, in response to receiving the token, restoring the user-selectable item to a selectable state.

DETAILED DESCRIPTION

Figure 1:
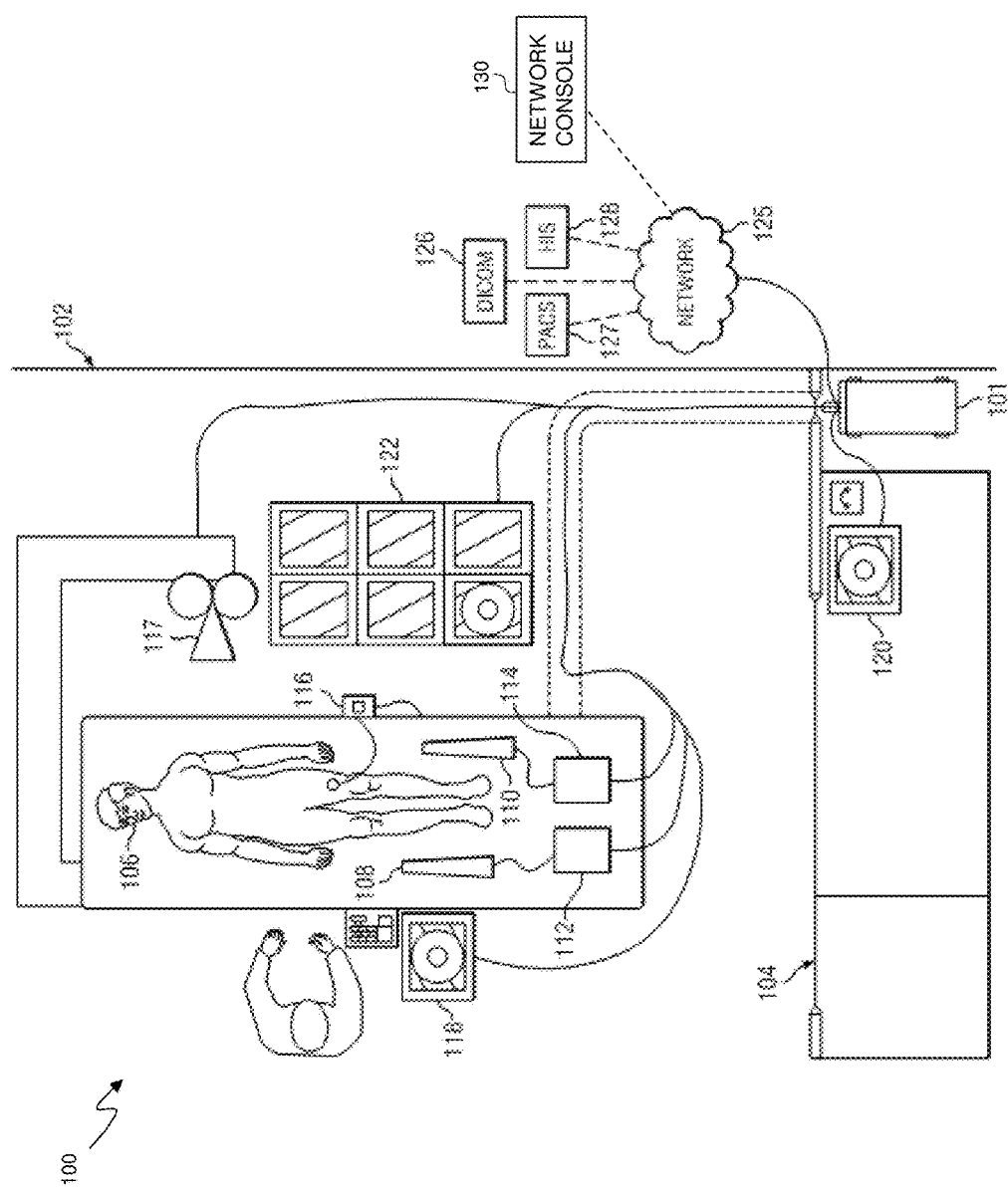
FIG. 1 is a schematic drawing depicting a medical system including a multi-modality processing system according to one embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic drawing depicting a medical system 100 including a multi-modality processing system 101 according to one embodiment of the present disclosure. In general, the medical system 100 provides for coherent integration and consolidation of multiple forms of acquisition and processing elements designed to be sensitive to a variety of methods used to acquire and interpret human biological physiology and morphological information and coordinate treatment of various conditions. More specifically, in system 100, the multi-modality processing system 101 is an integrated device for the acquisition, control, interpretation, and display of multi-modality medical sensing data. In one embodiment, the processing system 101 is a computer system with the hardware and software to acquire, process, and display multi-modality medical data, but, in other embodiments, the processing system 101 may be any other type of computing system operable to process medical data. In the embodiments in which processing system 101 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller or wireless communication controller. In that regard, in some particular instances the processing system 101 is programmed to execute steps associated with the data acquisition and analysis described herein. Accordingly, it is understood that any steps related to data acquisition, data processing, instrument control, and/or other processing or control aspects of the present disclosure may be implemented by the processing system using corresponding instructions stored on or in a non-transitory computer readable medium accessible by the processing system. In some instances, the processing system 101 is portable (e.g., handheld, on a rolling cart, etc.). Further, it is understood that in some instances processing system 101 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In the illustrated embodiment, the medical system 100 is deployed in a catheter lab 102 having a control room 104, with the processing system 101 being located in the control room. In other embodiments, the processing system 101 may be located elsewhere, such as in the catheter lab 102, in a centralized area in a medical facility, or at an off-site location (i.e., in the cloud). The catheter lab 102 includes a sterile field generally encompassing a procedure area but its associated control room 104 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination including an instantaneous wave-free ratio (iFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, x-ray angiography (XA), or any other medical sensing modalities known in the art. Further, the catheter lab and control room may be used to perform one or more treatment or therapy procedures on a patient such as radiofrequency ablation (RFA), cryotherapy, atherectomy or any other medical treatment procedure known in the art. For example, in catheter lab 102 a patient 106 may be undergoing a multi-modality procedure either as a single procedure or in combination with one or more sensing procedures. In any case, the catheter lab 102 includes a plurality of medical instruments including medical sensing devices that may collect medical sensing data in various different medical sensing modalities from the patient 106.

In the illustrated embodiment of FIG. 1, instruments 108 and 110 are medical sensing devices that may be utilized by a clinician to acquire medical sensing data about the patient 106. In a particular instance, the device 108 collects medical sensing data in one modality and the device 110 collects medical sensing data in a different modality. For instance, the instruments may each collect one of pressure, flow (velocity), images (including images obtained using ultrasound (e.g., IVUS), OCT, thermal, and/or other imaging techniques), temperature, and/or combinations thereof. The devices 108 and 110 may be any form of device, instrument, or probe sized and shaped to be positioned within a vessel, attached to an exterior of the patient, or scanned across a patient at a distance.

In the illustrated embodiment of FIG. 1, instrument 108 is an IVUS catheter 108 that may include one or more sensors such as a phased-array transducer to collect IVUS sensing data. In some embodiments, the IVUS catheter 108 may be capable of multi-modality sensing such as IVUS and IVPA sensing. Further, in the illustrated embodiment, the instrument 110 is an OCT catheter 110 that may include one or more optical sensors configured to collect OCT sensing data. In some instances, an IVUS patient interface module (PIM) 112 and an OCT PIM 114 respectively couple the IVUS catheter 108 and OCT catheter 110 to the medical system 100. In particular, the IVUS PIM 112 and the OCT PIM 114 are operable to respectively receive medical sensing data collected from the patient 106 by the IVUS catheter 108 and OCT catheter 110 and are operable to transmit the received data to the processing system 101 in the control room 104. In one embodiment, the PIMs 112 and 114 include analog to digital (A/D) converters and transmit digital data to the processing system 101, however, in other embodiments, the PIMs transmit analog data to the processing system. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, or some other high-speed data bus connection. In other instances, the PIMs may be connected to the processing system 101 via wireless connections using IEEE 802.11 Wi-Fi standards, Ultra Wide-Band (UWB) standards, wireless FireWire, wireless USB, or another high-speed wireless networking standard.

Additionally, in the medical system 100, an electrocardiogram (ECG) device 116 is operable to transmit electrocardiogram signals or other hemodynamic data from patient 106 to the processing system 101. In some embodiments, the processing system 101 may be operable to synchronize data collected with the catheters 108 and 110 using ECG signals from the ECG 116. Further, an angiogram system 117 is operable to collect x-ray, computed tomography (CT), or magnetic resonance images (MRI) of the patient 106 and transmit them to the processing system 101. In one embodiment, the angiogram system 117 may be communicatively coupled to the processing system to the processing system 101 through an adapter device. Such an adaptor device may transform data from a proprietary third-party format into a format usable by the processing system 101. In some embodiments, the processing system 101 may be operable to co-register image data from angiogram system 117 (e.g., x-ray data, MRI data, CT data, etc.) with sensing data from the IVUS and OCT catheters 108 and 110. As one aspect of this, the co-registration may be performed to generate three-dimensional images with the sensing data.

A bedside controller 118 is also communicatively coupled to the processing system 101 and provides user control of the particular medical modality (or modalities) being used to diagnose the patient 106. In the current embodiment, the bedside controller 118 is a touch screen controller that provides user controls and diagnostic images on a single surface. In alternative embodiments, however, the bedside controller 118 may include both a non-interactive display and separate controls such as physical buttons and/or a joystick. In the integrated medical system 100, the bedside controller 118 is operable to present workflow control options and patient image data in graphical user interfaces (GUIs). As will be described in greater detail in association with FIG. 2, the bedside controller 118 includes a user interface (UI) framework service through which workflows associated with multiple modalities may execute. Thus, the bedside controller 118 is capable of displaying workflows and diagnostic images for multiple modalities allowing a clinician to control the acquisition of multi-modality medical sensing data with a single interface device.

A main controller 120 in the control room 104 is also communicatively coupled to the processing system 101 and, as shown in FIG. 1, is adjacent to catheter lab 102. In the current embodiment, the main controller 120 is similar to the bedside controller 118 in that it includes a touch screen and is operable to display multitude of GUI-based workflows corresponding to different medical sensing modalities via a UI framework service executing thereon. In some embodiments, the main controller 120 may be used to simultaneously carry out a different aspect of a procedure's workflow than the bedside controller 118. In alternative embodiments, the main controller 120 may include a non-interactive display and standalone controls such as a mouse and keyboard.

The medical system 100 further includes a boom display 122 communicatively coupled to the processing system 101. The boom display 122 may include an array of monitors, each capable of displaying different information associated with a medical sensing procedure. For example, during an IVUS procedure, one monitor in the boom display 122 may display a tomographic view and one monitor may display a sagittal view.

Further, the multi-modality processing system 101 is communicatively coupled to a data network 125. In the illustrated embodiment, the data network 125 is a TCP/IP-based local area network (LAN), however, in other embodiments, it may utilize a different protocol such as Synchronous Optical Networking (SONET), or may be a wide area network (WAN). The processing system 101 may connect to various resources via the network 125. For example, the processing system 101 may communicate with a Digital Imaging and Communications in Medicine (DICOM) system 126, a Picture Archiving and Communication System (PACS) 127, and a Hospital Information System (HIS) 128 through the network 125. Additionally, in some embodiments, a network console 130 may communicate with the multi-modality processing system 101 via the network 125 to allow a doctor or other health professional to access the aspects of the medical system 100 remotely. For instance, a user of the network console 130 may access patient medical data such as diagnostic images collected by multi-modality processing system 101, or, in some embodiments, may monitor or control one or more on-going procedures in the catheter lab 102 in real-time. The network console 130 may be any sort of computing device with a network connection such as a PC, laptop, smartphone, tablet computer, or other such device located inside or outside of a health care facility.

Additionally, in the illustrated embodiment, medical sensing tools in system 100 discussed above are shown as communicatively coupled to the processing system 101 via a wired connection such as a standard copper link or a fiber optic link, but, in alternative embodiments, the tools may be connected to the processing system 101 via wireless connections using IEEE 802.11 Wi-Fi standards, Ultra Wide-Band (UWB) standards, wireless FireWire, wireless USB, or another high-speed wireless networking standard.

One of ordinary skill in the art would recognize that the medical system 100 described above is simply an example embodiment of a system that is operable to collect diagnostic data associated with a plurality of medical modalities. In alternative embodiments, different and/or additional tools may be communicatively coupled to the processing system 101 so as to contribute additional and/or different functionality to the medical system 100.

Figure 2:
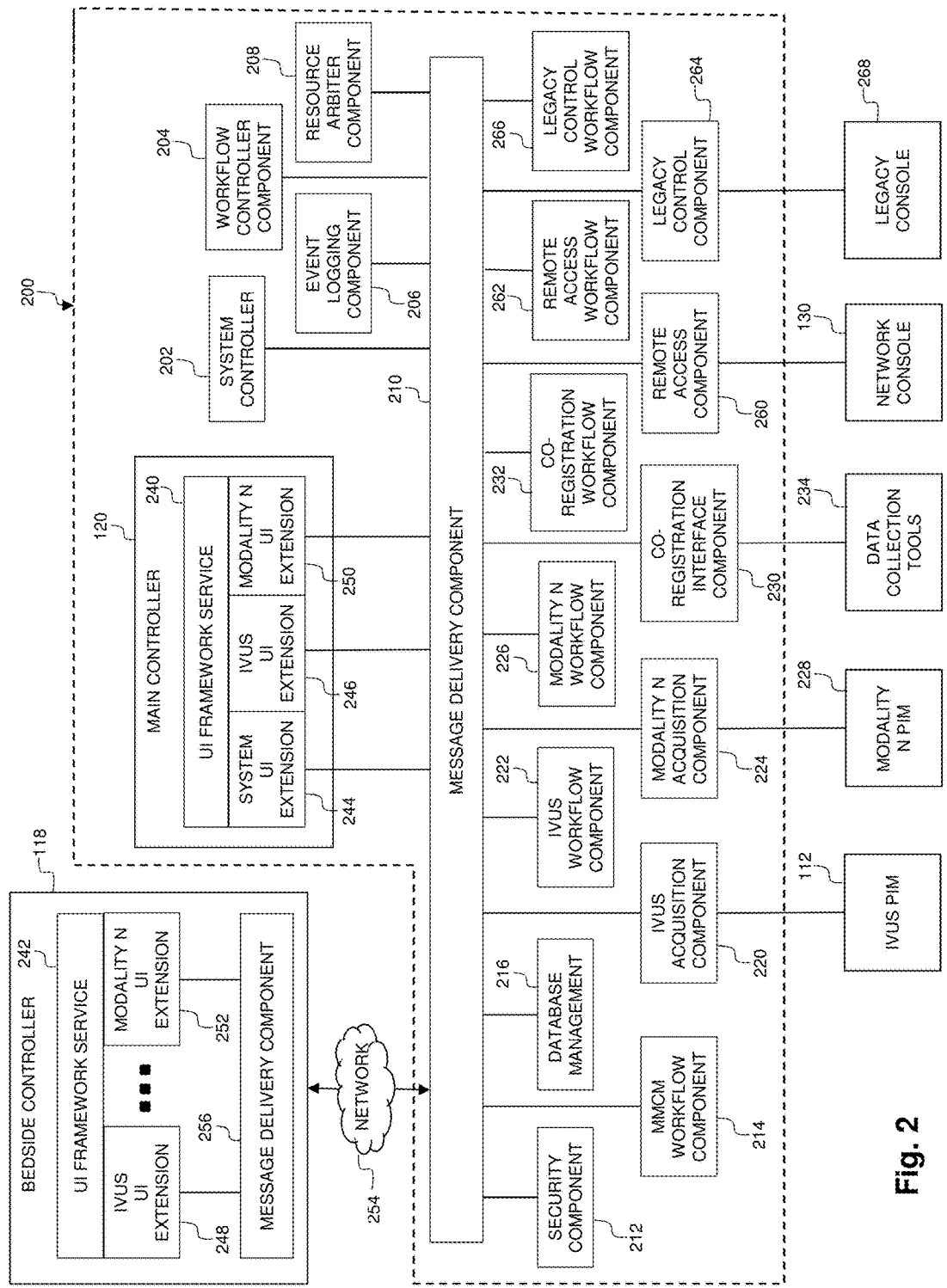
FIG. 2 is a functional block diagram of portions of the medical system, including a processing framework executing on an embodiment of the multi-modality processing system.

With reference now to FIG. 2, illustrated is a functional block diagram of portions of the medical system 100, including a processing framework 200 executing on an embodiment of the multi-modality processing system 101. The processing framework 200 includes various independent and dependent executable components that control the operation of the processing system 101, including the acquisition, processing, and display of multi-modality medical sensing data. In general, the processing framework 200 of processing system 101 is modular and extensible. That is, the framework 200 is comprised of independent software and/or hardware components (or extensions) respectively associated with different functions and medical sensing modalities. This modular design allows the framework to be extended to accommodate additional medical sensing modalities and functionality without impacting existing functionality or requiring changes to the underlying architecture. Further, an internal messaging system facilitates independent data communication between modules within the framework. In one instance, the processing framework 200 may be implemented as computer-executable instructions stored on a non-transitory computer-readable storage medium in the processing system 10. In other instances the processing framework 200 may be a combination of hardware and software modules executing within with the processing system 101.

Generally, in the embodiment shown in FIG. 2, processing framework 200 includes a plurality of components that are configured to receive medical sensing data from a plurality of medical sensing devices, process the data, and output the data as diagnostic images via the main controller 120, the bedside controller 118, or other graphical display device. The framework 200 includes several system-level components that manage the core system functions of the processing system 101 and also coordinate the plurality of modality-specific components. For instance, the framework 200 includes a system controller 202 that coordinates startup and shutdown of the plurality of executable components of the processing framework 200, including hardware and software modules related to acquisition and processing of patient diagnostic data. The system controller 202 is also configured to monitor the state of components executing within the framework 202, for instance, to determine if any components have unexpectedly stopped executing. In addition, the system controller 202 provides an interface through which other framework components may obtain system configuration and status information. Because the software framework 200 is modular, the system controller 202 is independent of the components within the framework that it manages so that errors and changes made to components do not affect the execution or structure of the system controller.

As mentioned above, the framework 200 is configured such that various extensions may be added and removed without system architecture changes. In certain embodiments, an extension executing within framework 200 may include a plurality of executable components that together implement the full functionality of the extension. In such embodiments, an extension may include an extension controller that is similar to the system controller 202 that is operable to startup, shutdown, and monitor the various executable components associated with the extension. For example, upon system startup, the system controller 202 may start an extension controller corresponding to a medical modality, and then the extension controller may, in turn, start the executable components associated with the modality. In one embodiment, extension controllers may be unallocated until system controller 202 associates them with a specific modality or other system task via parameters retrieved from a configuration mechanism, such as a configuration file.

The processing framework 200 further includes a workflow controller component 204 that is generally configured to govern the execution of the executable components of the framework 202 during multi-modality medical sensing workflows. For example, in one embodiment, the workflow controller component 204 controls executing components via a set of workflow rules that define the states in which the components may be, the actions that are permitted while components are in specific states, the conditions under which components may transition from one state to another, and the actions to be performed as part of such transitions. Stated differently, the processing framework 200, as governed by the workflow rules of the workflow controller component 204 may be implemented as a finite state machine in certain embodiments. In alternative embodiments, the workflow controller component 204 may govern workflows executed by the processing framework 200 in an alternative manner.

The processing framework 200 further includes an event logging component 206 that is configured to log messages received from various components of the processing framework. For instance, during system startup, the system controller 202 may send messages about the status of components being started to the event logging component 206 which, in turn, writes the messages to a log file in a standardized format. Additionally, the processing framework 200 includes a resource arbiter component 208 that is configured to manage the sharing of limited system resources between various executable components of the framework 202 during multi-modality medical sensing and/or treatment workflows. For example, during a multi-modality workflow, two or more components associated with different modalities within the processing framework 202 may be vying for the same system resource such as a graphical display on the main controller 120. In certain embodiments, the resource arbiter component 208 may implement a token-based resource sharing framework, in which components may request a token associated with a specific resource, hold the token while using the resource, and return the token when finished with the resource so that other components may subsequently request the token. In alternative embodiments, however, the resource arbiter component 208 may coordinate sharing of limited system resources in additional and/or different manners such as through a queue system or a hierarchical collision management system. Further, in one embodiment, the resource arbiter component 208 may include a synchronization library of function calls that the various modality components may access in order to synchronize their operation.

In one embodiment, the system controller 202, workflow controller component 204, event logging component 206, and resource arbiter component 208 may be implemented as processor-executable software stored on non-transitory, computer-readable storage medium, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software. In certain embodiments in which executable components are implemented in FPGAs, the system controller 202 may be configured to dynamically alter the programmable logic within the FPGAs to implement various functionality needed at the time. As an aspect of this, the processing system 101 may include one or more unassigned FPGAs that may be allocated by the system controller during system startup. For instance, if upon startup of the processing system 101, the system controller detects an OCT PIM and catheter coupled thereto, the system controller or an extension controller associated with OCT functionality may dynamically transform the programmable logic within one the unassigned FPGAs such that it includes functionality to receive and/or process OCT medical data.

To facilitate intersystem communication between different hardware and software components in the multi-modality processing system 101, the processing framework 200 further includes a message delivery component 210. In one embodiment, the message delivery component 210 is configured to receive messages from components within the framework 202, determine the intended target of the messages, and deliver the messages in timely manner (i.e., the message delivery component is an active participant in the delivery of messages). In such an embodiment, message metadata may be generated by the sending component that includes destination information, payload data (e.g., modality type, patient data, etc), priority information, timing information, or other such information. In another embodiment, message delivery component 210 may be configured to receive messages from components within the framework 202, temporarily store the messages, and make the messages available for retrieval by other components within the framework (i.e., the message delivery component is a passive queue). In any case, the message delivery component 210 facilitates communication between executable components in the framework 200. For instance, the system controller 202 may utilize the message delivery component 210 to inquire into the status of components starting up during a system startup sequence, and then, upon the receiving status information, utilize the message delivery component to transmit the status information to the event logging component 206 so that it may be written to a log file. Similarly, the resource arbiter component 208 may utilize the message delivery component 210 to pass a resource token between components requesting access to limited resources.

In one example embodiment in which the message delivery component 210 is a passive queue, components in the framework 200 may packetize incoming medical sensing data into messages and then transmit the messages to a queue on the message delivery component where they may be retrieved by other components such as image data processing components. Further, in some embodiments, the message delivery component 210 is operable to make received messages available in a First-In-First-Out (FIFO) manner, wherein messages that arrive on the queue first will be removed from the queue first. In alternative embodiments, the message delivery component 210 may make messages available in a different manner for instance by a priority value stored in a message header. In one embodiment, the message delivery component 210 is implemented in random-access memory (RAM) in the processing system 101, but, in other embodiments, it may be implemented in non-volatile RAM (NVRAM), secondary storage (e.g., magnetic hard drives, flash memory, etc), or network-based storage. Further, in one embodiment, messages stored on the message delivery component 210 may be accessed by software and hardware modules in processing system 101 using Direct Memory Access (DMA).

The processing framework 202 further includes a number of additional system components that provide core system functionality including a security component 212, a multi-modality case management (MMCM) component 214, and a database management component 216. In certain embodiments, the security component 212 is configured to provide various security services to the overall processing framework and to individual components. For example, components implementing an IVUS data acquisition workflow may utilize encryption application programming interfaces (APIs) exposed by the security component 212 to encrypt IVUS data before it is transmitted over a network connection. Further, the security component 212 may provide other security services, such as system-level authentication and authorization services to restrict access to the processing framework to credentialed users and also to prevent the execution of untrusted components within the extensible framework. The multi-modality case management (MMCM) component 214 is configured to coordinate and consolidate diagnostic data associated with a plurality of medical modalities into a unified patient record that may be more easily managed. Such a unified patient record may be more efficiently stored in a database and may be more amenable to data archival and retrieval. In that regard, the database management component 216 is configured to present transparent database services to the other components in the framework 200 such that database connection and management details are hidden from the other components. For example, in certain embodiments, the database management component 216 may expose an API that includes database storage and retrieval functionality to components of the framework 200. In other words, a medical sensing workflow component may be able to transmit diagnostic data to a local and/or remote database such as a DICOM or PACS server via the database component without being aware of database connection details. In other embodiments, the database management component 216 may be operable perform additional and/or different database services such as data formatting services that prepare diagnostic data for database archival.

As mentioned above, the processing framework 200 of the multi-modality processing system 101 is operable to receive and process medical data associated with a plurality of modalities. In that regard, the processing framework 200 includes a plurality of modular acquisition components and workflow components that are respectively associated with different medical sensing and diagnostic modalities. For instance, as shown in the illustrated embodiment of FIG. 2, the processing framework 200 includes an IVUS acquisition component 220 and an IVUS workflow component 222 that are respectively configured to receive and process IVUS medical sensing data from the IVUS PIM 112. In accordance with the modular and extensible nature of the processing framework 200, any number of additional acquisition and workflow components may be independently added to the framework as denoted by the modality "N" acquisition component 224 and the modality "N" workflow component 226 that acquire and process data from a modality "N" PIM 228. For example, in certain embodiments, the processing system 101 may be communicatively coupled to the OCT PIM 114, the ECG system 116, a fractional flow reserve (FFR) PIM, a FLIVUS PIM, and an ICE PIM. In other embodiments, additional and/or different medical sensing, treatment, or diagnostic devices may be coupled to the processing system 101 via additional and/or different data communication connections known in the art. In such a scenario, in addition to the IVUS acquisition module 220, the processing framework 200 may include an FFR acquisition component to receive FFR data from an FFR PIM, a FLIVUS acquisition component to receive FLIVUS data from a FLIVUS PIM, an ICE acquisition component to receive ICE data from an ICE PIM, and an OCT acquisition component is operable to receive OCT data from an OCT PIM. In this context, medical data communicated between the executable components of the processing framework 200 and the communicatively coupled medical devices (e.g., PIMs, catheters, etc) may include data collected by sensors, control signals, power levels, device feedback, and other medical data related to a sensing, treatment, or diagnostic procedure. Further, in certain embodiments, patient treatment devices may be communicatively coupled to the processing system 101 such as devices associated with radiofrequency ablation (RFA), cryotherapy, or atherectomy and any PIMs or other control equipment associated with such treatment procedures. In such an embodiment, the modality "N" acquisition component 224 and the modality "N" workflow component 226 may be configured to communicate with and control the treatment devices such as by relaying control signals, relaying power levels, receiving device feedback, and receiving data collected by sensors disposed on the treatment devices.

In one embodiment, once the acquisition components 220 and 224 have received data from connected medical sensing devices, the components packetize the data into messages to facilitate intersystem communication. Specifically, the components may be operable to create a plurality of messages from an incoming digital data stream, where each message contains a portion of the digitized medical sensing data and a header. The message header contains metadata associated with the medical sensing data contained within the message. Further, in some embodiments, the acquisition components 220 and 224 may be operable to manipulate the digitized medical sensing data in some way before it is transmitted to other portions of the framework 200. For example, the acquisition components may compress the sensing data to make intersystem communication more efficient, or normalize, scale or otherwise filter the data to aid later processing of the data. In some embodiments, this manipulation may be modality-specific. For example, the IVUS acquisition component 220 may identify and discard redundant IVUS data before it is passed on to save processing time in subsequent steps. The acquisition components 220 and 224 may additionally perform a number of tasks related to the acquisition of data including responding to interrupts generated by data buses (e.g., PCIe, USB), detecting which medical sensing devices are connected to processing system 101, retrieving information about connected medical sensing devices, storing sensing device-specific data, and allocating resources to the data buses. As mentioned above, the data acquisition components are independent from each other and may be installed or removed without disrupting data acquisition by other components. Additionally, acquisition components are independent of underlying data bus software layers (for example, through the use of APIs) and thus may be created by third parties to facilitate acquisition of data from third party medical sensing devices.

The workflow components of the processing framework, such as the IVUS workflow component 222, receive unprocessed medical sensing and/or diagnostic data from respective acquisition components via the message delivery component 210. In general, the workflow components are configured to control the acquisition of medical sensing data such as by starting and stopping data collection at calculated times, displaying acquired and processed patient data, and facilitating the analysis of acquired patient data by a clinician. As an aspect of this, the workflow components are operable to transform unprocessed medical data gathered from a patient into diagnostic images or other data formats that enable a clinician to evaluate a patient's condition. For example, an IVUS workflow component 222 may interpret IVUS data received from the IVUS PIM 112 and convert the data into human-readable IVUS images. In one embodiment, a software stack within the framework may expose a set of APIs with which the workflow component 222 and other workflow components in the framework may call to access system resources such as the computational resources, the message delivery component 210, and communication resources. After processing acquired data, the modality-centric workflow components may transmit one or messages containing the processed data to other components within the framework 200 via the message delivery component 210. In some embodiments, before sending such messages, the components may insert a flag in the header indicating that the message contains processed data. Additionally, in some embodiments, after processing medical sensing data, the components may utilize the database management component 216 to transmit the processed data to archival systems such as a locally attached mass storage device or the network-based PACS server 127. In accordance with the modular architecture of the processing framework 200, the workflow components 222 and 226 are independent of each other and may be installed or removed without disrupting other components, and may be written by third parties. Further, due to their independence, they may be are operable to process signaling and imaging data from multiple medical sensing devices concurrently.

The processing framework 200 additionally includes a co-registration interface component 230 and a co-registration workflow component 232 that are configured to acquire and process data from any number of data collection tools 234 and co-register the acquired data with data acquired by one of the other acquisition components within the framework. In more detail, the co-registration interface component 230 may be operable to communicatively interface with medical data acquisition tools associated with any number of modalities, such as the ECG device 116 or the angiography system 117 of FIG. 1. In certain embodiments, the interface component 230 may be operable to standardize and/or transform incoming modality data such that it may be co-registered with other sensing data acquired by the processing system 101. As medical data is being acquired by the co-registration interface component 230, the co-registration workflow component 232 is configured to facilitate the co-registration of data from different modalities such as by spatially or temporally synchronizing data collection among medical sensing devices, aligning two or more acquired data sets based on spatial or temporal registration markers, and generating co-registered diagnostic images or other human-readable data that enable a clinician to evaluate a patient's condition. Further, in other embodiments, the co-registration workflow component 232 may be operable to spatially co-register catheter-gathered data in a two-dimensional (2-D) or three-dimensional (3-D) space using previously-generated 2-D images or 3-D models. For example, a catheter-based sensing tool may include fiducials that are tracked to generate position data during a sensing procedure, and the co-registration workflow component 232 may register this position data against previously acquired MRI data. Still further, the co-registration workflow component 232 may facilitate co-registration of multi-modality data acquired by native acquisition components within the framework 200 such as the IVUS acquisition component 220 and modality "N" acquisition component 224. Additionally, in some embodiments, a real-time clock may be integrated into the co-registration workflow component 232. U.S. Provisional Patent Application No. 61/473,591, entitled "DISTRIBUTED MEDICAL SENSING SYSTEM AND METHOD", discloses temporally synchronizing medical sensing data collection in more detail and is hereby incorporated by reference in its entirety.

As discussed above in association with FIG. 1, a clinician utilizing the processing system 101 may control workflows and view diagnostic images through the main controller 120 and the bedside controller 118. The main controller 120 and the bedside controller 118 respectively include user interface (UI) framework services 240 and 242 that support a plurality of user interface (UI) extensions (or components). In general, the UI extensions supported by the UI framework services 240 and 242 respectively correspond to medical sensing modalities and are operable to render a user interface for control of the associated acquisition workflow and display of processed sensing data. Similar to the processing framework 200, the UI frameworks 240 and 242 are extensible in that they support UI extensions that are independent of one another. That is, its modular design allows the UI frameworks 240 and 242 to be extended to accommodate additional medical sensing modality user interfaces without impacting existing user interfaces or requiring changes to the underlying UI architectures. In the illustrated embodiment, the main controller 120 includes a system UI extension 244 that renders a user interface containing core system controls and configuration options. For example, a clinician may startup, shutdown or otherwise manage the processing system 101 using the user interface rendered by the system UI extension 244. In one embodiment, the components of the main controller 120 may be considered part of the processing framework 200. The IVUS UI extensions 246 and 248 render user interfaces for the main controller 120 and bedside controller 118, respectively. For example, the IVUS UI extensions 246 and 248 may render and display the touch screen buttons used to control an IVUS workflow and also render and display the IVUS diagnostic images created by the IVUS workflow component 222. Similarly, the modality "N" UI extensions 250 and 252 render controls and images associated with a modality "N" workflow.

In one embodiment, the UI framework services 240 and 242 may expose APIs with which the UI extensions may call to access system resources such as a look-and-feel toolbox and error handling resources. Look-and-feel toolbox APIs enable the UI extensions to present a standardized user interface with common buttons, parallel workflow formats, and data presentation schemes for different modality workflows. In this manner, clinicians may more easily transition between acquisition modalities without additional user interface training. Further, co-registration UI extensions may present and/or combine processed image or signaling data from multiple modalities. For instance, a UI extension may display an electrocardiogram (ECG) wave adjacent to IVUS imaging data or may display an IVUS image overlaid with borders that were previously drawn on an OCT image. Further, in some embodiments, the UI framework services 240 and 242 may include a multi-tasking framework to coordinate concurrently executing UI extensions. For instance, in the event the processing system 101 is simultaneously acquiring data associated with more than one modality, the UI framework services 240 and 242 may present the user with a modality selector screen on which a desired user interface may be selected.

The UI framework service 240 communicates with the components of the processing framework 200 via the message delivery component 210. As shown in the illustrated embodiment of FIG. 2, the bedside controller 118 may be communicatively coupled to the processing framework 200 via a network connection 254. The network connection 254 may be any type of wired of wireless network connection such as an Ethernet connection or IEEE 802.11 Wi-Fi connection. Alternatively, one or both of the main and bedside controllers 120 and 118 may communicate with the processing framework 200 via a local bus connection such as a (PCIe) data bus connection, a USB connection, a Thunderbolt connection, a FireWire connection, or some other high-speed data bus connection. Further, in the illustrated embodiment of FIG. 2, the bedside controller includes a message delivery component 256 that is configured to facilitate message-based communication between the UI extensions in the bedside controller 118 and the components in the processing framework 200. In certain embodiments, the message delivery component 256 may extract diagnostic image data from network communication packets as they arrive over the network connection 254.

The processing framework 200 includes additional components that allow a clinician to access and/or control workflows executing in the multi-modality processing system 101. For example, the framework 200 includes a remote access component 260 that communicatively couples the network console 130 (FIG. 1) to the processing framework 200. In one embodiment, the remote access component 260 is operable to export control functionality of the processing system 101 to the network console 130, so that the network console may present workflow control functions in its user interface. In certain embodiments, the remote access component 260 may receive workflow commands from the network console 130 and forward them to a remote access workflow component 262. The remote access workflow component 262 may dictate the set of commands and diagnostic data to which a remote user may access through the network console 130. Further, the legacy control component 264 and legacy control workflow component 266 provide some level of access to modality workflow control and data to users of legacy consoles 268 (e.g. button consoles, mice, keyboards, standalone monitors).

In one embodiment, the core system components of the processing framework 200 and the additional components such as the modality-related components may be implemented as processor-executable software stored on non-transitory, computer-readable storage medium, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software.

One of ordinary skill in the art will recognize that the processing framework 200 of FIG. 2 is simply an example embodiment and, in alternative embodiments, the framework may include different and/or additional components configured to carry out various medical sensing workflows. For instance, the processing framework 200 may further include executable components configured for the evaluation of a stenosis of a human blood vessel or configured to facilitate control of computer-assisted surgery or remotely-controlled surgery.

As described above, multi-modality processing systems like system 101 may include a plurality of modality components that utilize shared resources within the processing system. When a plurality of modality components are operating within the processing system 101, coordination between the components may be necessary when synchronous behavior is desired. This is because the independent modality components are, by their nature, asynchronous. In the processing system 101, synchronous operation between the independent modality components is coordinated through the resource arbiter component 208. For example, the resource arbiter component 208 in the illustrated embodiment is a library of function calls available to the modality components that enable them to communicate to other components when shared resources are needed or an action affecting patient safety will be carried out. In the embodiments associated with FIGS. 3-9, the resource arbiter component 208 implements a token-based resource sharing framework for the coordination of modality components within the processing system 101. In alternative embodiments, however, the resource arbiter component 208 may coordinate sharing of limited system resources in additional and/or different manners such as through a queue system or a hierarchical collision management system.

Figure 3:
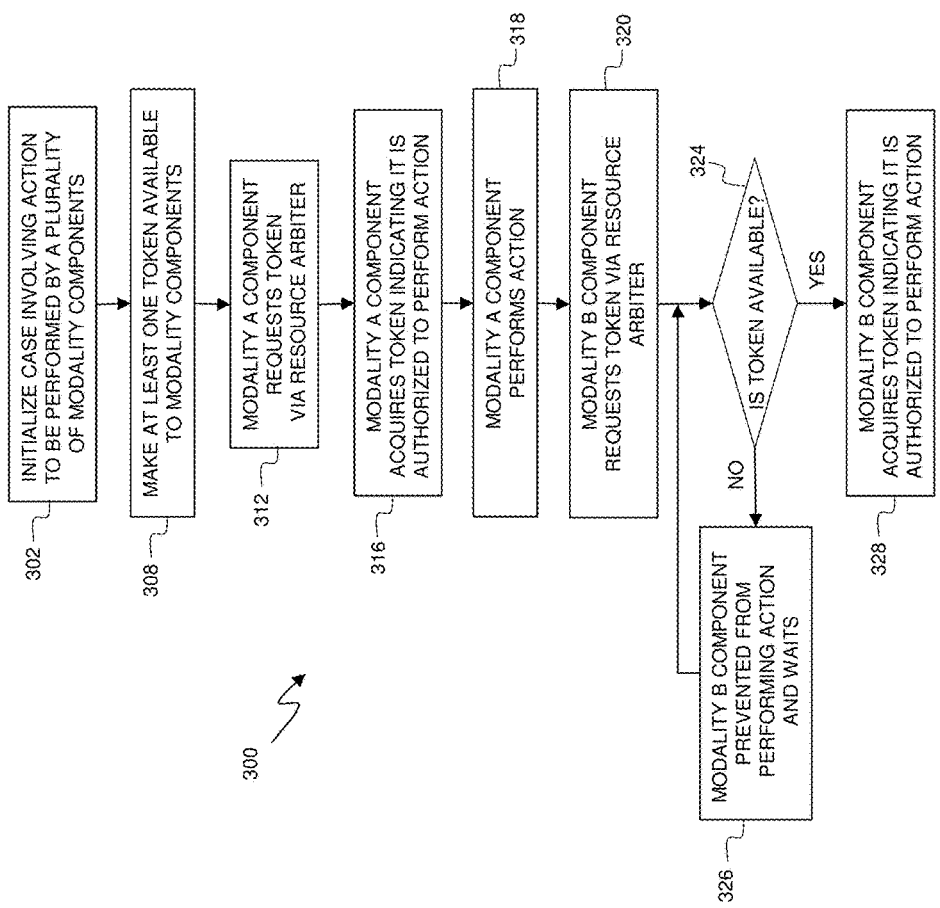
FIG. 3 is a high-level flowchart illustrating a method for resource management in a multi-modality medical processing system according to aspects of the present disclosure.

Referring now to FIG. 3, illustrated is a high-level flowchart illustrating a method 300 for resource management in a multi-modality medical processing system according to aspects of the present disclosure. In the illustrated embodiment, a token passing scheme is utilized to synchronize resource usage and actions performed by multiple, independent modality components. In the illustrated embodiment, at least a portion of the method 300 is carried out by various components of the processing framework 200 of FIG. 2. Further, in one embodiment, portions of the method 300 may be implemented as computer-readable instructions stored on a mass storage device or system memory and executed by a processor of the multi-modality processing system 101 of FIG. 1. Further, the method 300 in FIG. 3 is a high-level overview and details associated with various blocks in the method will be described in association with subsequent figures in the present disclosure.

The method 300 begins at block 302 where a case associated with a patient undergoing a multi-modality medical procedure is initialized. In this context, a case is associated within a particular patient. Initializing a case may include creating and opening a new case by collecting patient information or it may include retrieving and opening a previously created case. After a case has been initialized, the multi-modality procedure may begin on the patient associated with the case. In the illustrated embodiment, the multi-modality procedure includes a diagnostic and/or treatment-related action to be performed by more than one of the plurality of modality components within the multi-modality processing system 101. The action may be any number of actions that require some level of coordination between multiple modality components. For example, the action could be the energizing a medical instrument inside of a patient for therapeutic or imaging purposes where only one medical instrument may be activated at a time, or it could be presenting acquired patient images on a display screen where only data from one modality may be presented at a time. Another example of a serial multi-modality workflow is the initial use of iFR/FFR to ascertain the treatment necessary for an identified lesion in a patient's vessel, and the subsequent use of IVUS to visualize the installation of a stent in the vessel. For the general purpose of illustrating the method 300 shown in FIG. 3, the action is energizing a medical instrument in a multi-modality procedure where only one medical instrument may be energized at a time.

Figure 4:
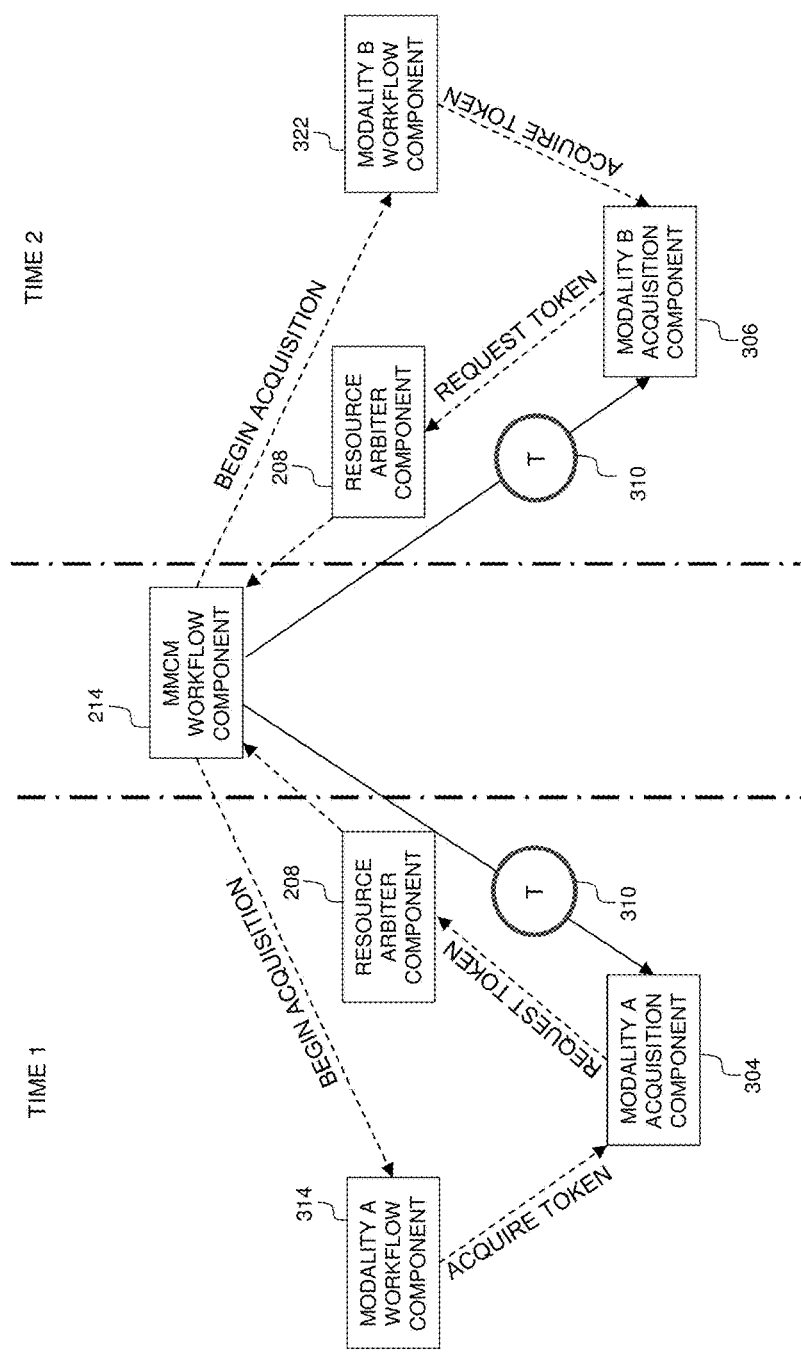
FIG. 4 is a simplified block diagram of a portion of a multi-modality procedure where a first modality component performing data acquisition at a time 1 and second modality component is performing data acquisition at a time 2.

In this regard, FIG. 4 is a simplified block diagram of a portion of a multi-modality procedure where a first modality component performs data acquisition at a time 1 and second modality component performs data acquisition at a time 2 (i.e., in a serial manner). In this example, an acquisition component 304 associated with modality A controls the energy applied to a transducer at the end of a guide wire inserted into a patient's vessel. An acquisition component 306 associated with modality B controls energy applied to a transducer affixed to a catheter inserted into the vessel over the guide wire. This instrument configuration has the potential for delivering energy to the same location by activating both wire and catheter transducers simultaneously. In some multi-modality procedures, energy must be applied to the transducers in a serial fashion so as to avoid simultaneous activation. In such a case, the method 300 ensures that only one of modality A component 304 and modality B component 306 may activate their transducer at a given time.

Referring back to FIG. 3, after a case associated with a patient has been initialized, the method 300 moves to block 308 where one or more tokens are made available to the plurality of modality components. Possession of a token is representative of authorization to perform an action, and lack of possession of a token is representative of a lack of authorization to perform an action. In the example scenario presented above, a modality component in possession of a token may energize its transducer, but a modality component not in possession of a token may not energize its transducer. In other words, if there is only one token associated with an action, the modality component in possession of the token is granted a mutual exclusion lock (or mutex) over the resources associated with the action. In the example workflow of FIG. 4, the MMCM workflow component holds a single token 310 that represents the authority to acquire patient data by energizing a transducer. In other embodiments, a greater number of tokens may be made available in association with the action of energizing transducers. For example, in some multi-modality workflows, multiple modalities may be authorized to energize their respective instruments concurrently.

Further, in certain embodiments, tokens are only available to modality components when a patient case is open, and tokens must be returned when a patient case is closed. This ensures that no medical data is erroneously added to a "closed" patient case. Additionally, if a patient case is closed abruptly during a procedure, any tokens held by modality components would be revoked immediately to terminate any ongoing workflow actions (e.g., acquisition, display, treatment) associated with the case.

Once one or more tokens associated with an action are made available to modality components in block 308, the method 300 continues to block 312 where a first modality component requests the token. In certain embodiments, this token request may be made via the synchronization library of the resource arbiter component 208—for example, through a function call. When a token request is received by the resource arbiter, it may forward the request on to the module that holds the tokens, in this case the MMCM workflow component 214. By routing all token related actions through the resource arbiter component 208, the details of the token-based synchronization framework may be hidden from the individual modality components. In the example of FIG. 4, the MMCM workflow component 214 commands modality A workflow component 314 to begin data acquisition from a patient. The modality A workflow component 314, in turn, instructs the modality A acquisition component 304 to acquire a token and begin data acquisition by energizing a sensor within the patient. The modality A acquisition component 304 then sends a token request to the resource arbiter component 208, which determines which component within the processing system 101 holds the token 310 associated with the action of energizing a sensor within the patient. In the illustrated embodiment, the resource arbiter component 208 forwards the token request to the MMCM workflow component 214.

After a token request has been made in block 312, method 300 continues to block 316 where the token 310 is passed to the modality A acquisition component 304. As a result, in block 318, the acquisition component 304 may commence data acquisition on the patient. Notably, because there is only one token associated with the action of energizing an instrument within the patient, the other modality acquisition components, such as modality B acquisition component 306, may not energize any instruments under their control. In other words, the action is locked for the exclusive use of the modality A acquisition component 304. As mentioned above, the token may be associated with a shared resource, and thus, possession of the token represents locking the shared resource for exclusive use of the holder of the token. For example, if the shared resource is a viewport in which patient images are displayed, the viewport may be locked for the exclusive use by one modality component.

The resource arbiter component 208 is not limited to managing access to only the shared resources in the embodiments listed above. It is operable to manage access to any number and type of shared resources that may be included in multi-modality processing systems. For example, the resource arbiter component 208 may manage access to control point connections that have low or moderate (i.e., limited) bandwidth, memory buffers during streaming operations, and remote, network-based resources during data intensive activities such as diagnostic image review.

Method 300 next moves to block 320 where a second modality component requests the token via the resource arbiter component 208. In the example of FIG. 4, modality B workflow component 322 instructs the modality B acquisition component 306 to acquire a token, which, in turn, sends a request for the token 310 to the resource arbiter component 208. After a request for a token has been received, the method 300 moves to decision block 324 where it is determined whether a token associated with the requested action is available. For example, after a token request is received from the modality B acquisition component 306, the resource arbiter 208 determines if the MMCM workflow component currently holds the token 310. If the token 310 is currently in the possession of another modality component, such as modality A acquisition component 304, the resource arbiter component 208 informs the modality B acquisition component 306 that a token is not available in block 326. The modality B acquisition component 306 is thus prevented from energizing its transducer within the patient. In one embodiment, if a token request cannot be filled, the resource arbiter component 208 places the requester component in a queue and when a token becomes available, the token is automatically passed to the requester without it having to make another request. In another embodiment, if a token request cannot be filled, the requesting modality component is informed of the token status and periodically makes subsequent checks until the request is filled. In some embodiments, the modality component may also subscribe to a notification service that notifies the component of the token status. If in decision block 324 the requested token 310 is available, however, the method 300 moves to block 328 where the token is passed to the requesting modality B component.

One of ordinary skill in the art would understand that the term "token" as used in association with the present disclosure is simply representative of the concept of locking resources to achieve synchronous behavior as between independent modality components, and that other terms may be used to convey the same concept. For example, a "lock and key" metaphor may be used wherein a resource is locked by default and only the component with a key may access it. Similarly, it may simply be said that a mutex is utilized to achieve component synchronization.

Further, it is understood that the method 300 for resource management within a multi-modality processing system is simply an example embodiment, and in alternative embodiments, additional and/or different steps may be included in the method. For example, in one embodiment, the action authorized by the possession of the token may be a different action than acquiring data within a patient. For example, the action may be displaying patient imaging data on a display as it is being collected, or the action may be applying therapeutic treatments to particular patient that must be performed in a serial manner. Further, the specific components in the processing system 101 that handle token-related tasks may be different than those described in association with the example of FIG. 4. For example, an additional and/or different component than the MMCM workflow controller 214 may hold the tokens when they are not possessed by a modality component. Further, the resource arbiter component 208 may handle token requests in a different manner, for example, by routing a request directly to the component holding the tokens.

Additionally, the method 300 may additionally implement authorization checks when a request is received—for example, to determine if the requesting modality component is authorized to perform the action associated with the requested token. In some scenarios, certain modalities may not be used on a specific patient for regulatory reasons, and so, when a token request is received, if the component requesting the token is associated with an unauthorized modality, a token will not be passed to the component regardless of whether a token is available. Further, in certain embodiments, the number of tokens associated within a specific action may be dynamically increased or decreased depending on operating conditions or changes in workflow protocols. For example, due to a decrease in the amount of power required to energize imaging instruments, a multi-modality workflow may be altered to allow for the simultaneously collection of two types of modality imaging data. In such a case, the number of tokens associated with the workflow action may be increased from one to two or more. In other situations, the number of tokens may be dynamically decreased during a workflow—for example, in response to an emergency, as will be described in association with FIGS. 5 and 6.

Figure 5:
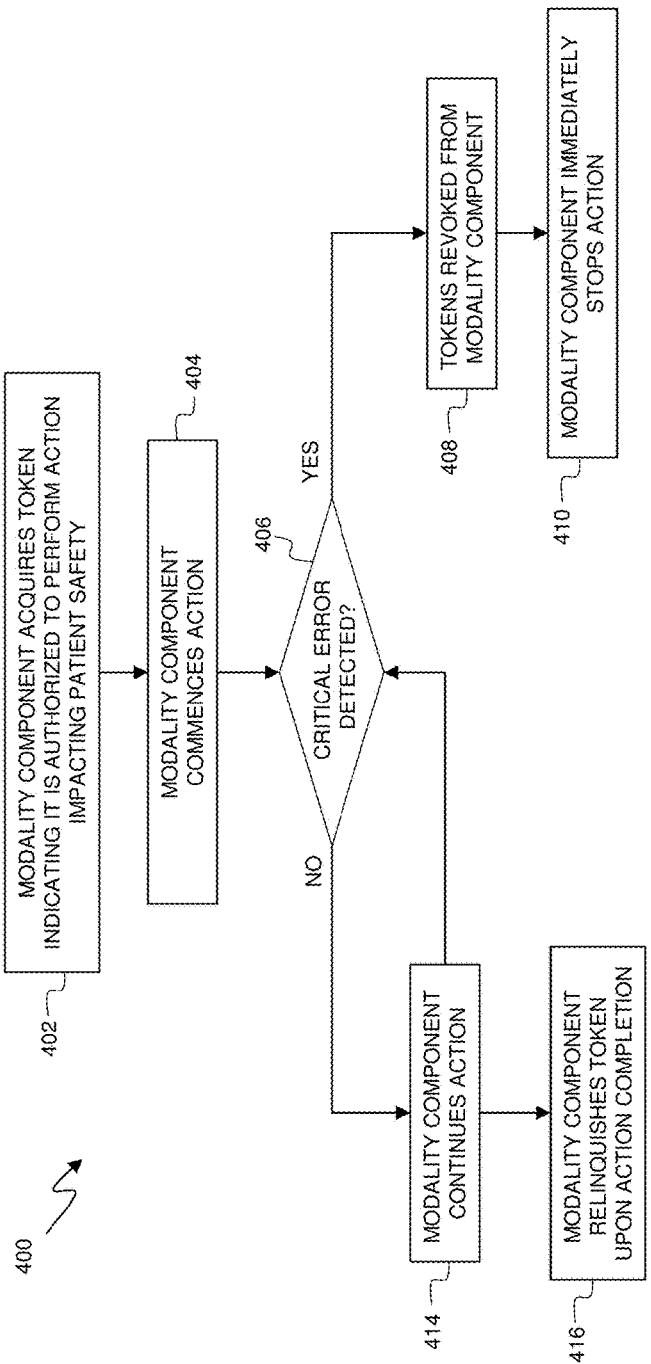
FIG. 5 is a high-level flowchart illustrating a method for error management in a medical processing system according to aspects of the present disclosure.

In that regard, FIG. 5 is a high-level flowchart illustrating a method 400 for error management in a medical processing system according to aspects of the present disclosure. In particular, the method 400 operates within the token-based framework described in association with FIGS. 3 and 4. During medical procedures on a patient, sometimes errors occur with respect some aspect of the workflow equipment or software. For patient safety reasons, a medical processing system should have in place a way to perform an emergency stop to prevent any harm from being inflicted on the patient. In processing system 101 of the present disclosure, an emergency stop may be executed through dynamic token revocation as implemented by method 400.

Figure 6:
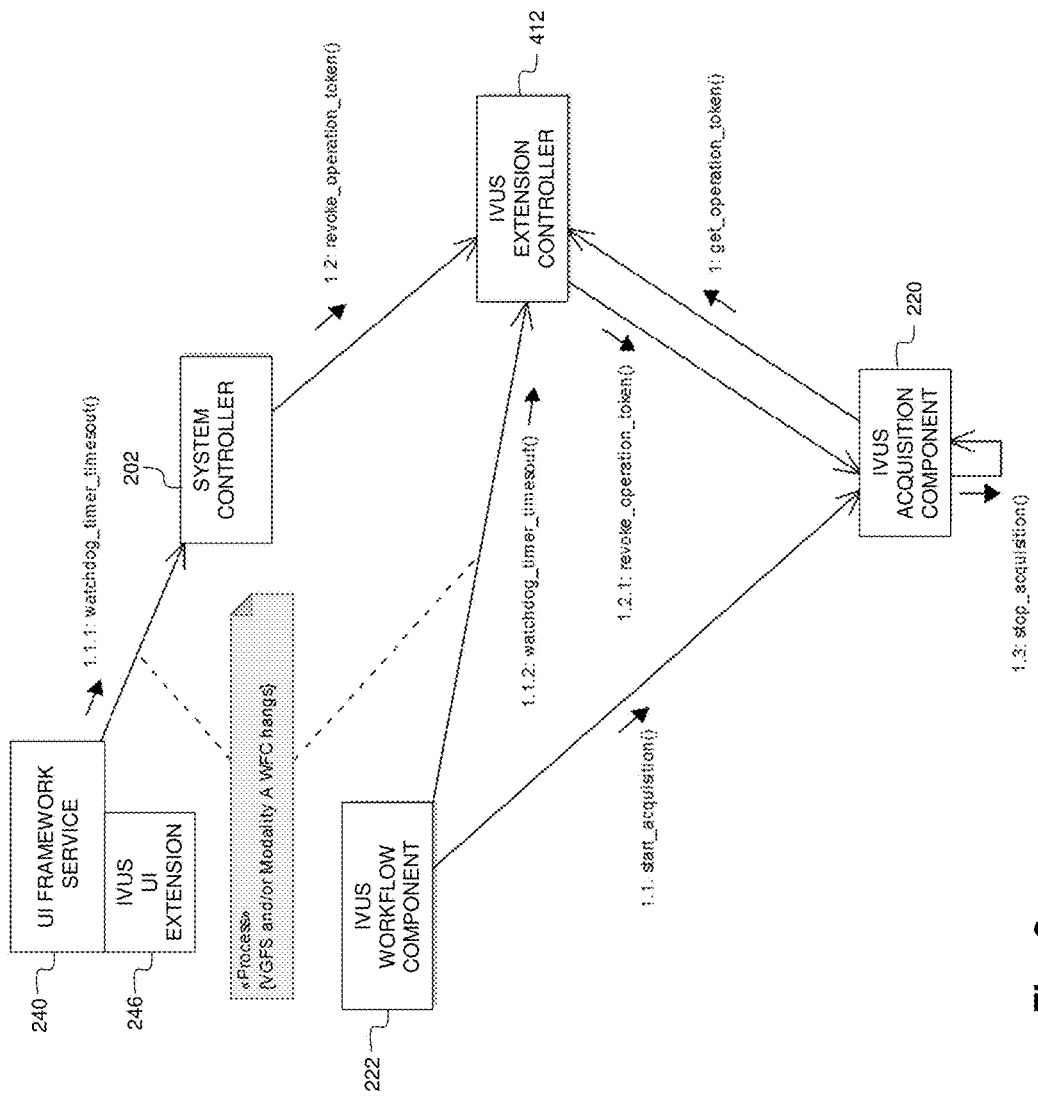
FIG. 6 is a simplified block diagram of a portion of a medical imaging procedure in which a critical error occurs and an emergency stop is needed to preserve patient safety.

In the illustrated embodiment, at least a portion of the method 400 is carried out by various components of the processing framework 200 of FIG. 2. Further, in one embodiment, portions of the method 400 may be implemented as computer-readable instructions stored on a mass storage device or system memory and executed by a processor of the multi-modality processing system 101 of FIG. 1. Further, the method 400 in FIG. 5 is a high-level overview and details associated with various blocks in the method will be described in association with subsequent figures in the present disclosure. In this regard, FIG. 6 is a simplified block diagram of a portion of a medical imaging procedure in which a critical error occurs within the multi-modality processing system 101 and an emergency stop is needed to preserve patient safety. In particular, the example medical imaging procedure in FIG. 6 is an IVUS imaging workflow in which an IVUS imaging instrument is capturing image data from within a patient and the image data is being displayed to a practitioner in real-time on a display associated with the processing system 101. In such a scenario, it is essential that the IVUS images are displayed to the practitioner so that the IVUS imaging instrument disposed within the patient may be safely maneuvered.

The method 400 begins at block 402 where a modality component acquires a token indicating that it is authorized to perform an action with some impact on patient safety. In the example of FIG. 6, the IVUS acquisition component 220 is commanded to begin image acquisition by the IVUS workflow controller 222 so it requests a token representing the authorization to energize an image sensor under its command. As mentioned in association with FIGS. 3 and 4, the token request may be handled by the resource arbiter component 208. If the requested token is available, it is passed to the IVUS acquisition component 220 so that it may begin image capture.

The method 400 next proceeds to block 404 where the modality component in possession of the token commences the action impacting patient safety. In the illustrated embodiment of FIG. 6, the IVUS acquisition component 220 energizes its imaging sensors and transmits the captured IVUS data to the IVUS UI extension 246 so that it may convert the data into images and display them in real-time on a display. As data acquisition is ongoing, the IVUS workflow controller 222 controls the duration, frequency, and other parameters of the IVUS data capture.

After the action impacting patient safety has commenced in block 404, the method 400 moves to decision block 406 where it is determined whether a critical error has occurred in in the context of the workflow that adversely affects patient safety. In the context of IVUS image acquisition, one example of a critical error is the user interface crashing so that the practitioner controlling the IVUS sensor within the patient is prevented from viewing real-time images. For example, the UI framework service 240 or the IVUS UI extension 246 may encounter a critical error that prevents IVUS data from being processed into images and displayed. In one embodiment, a watchdog timer tracks component activity and if the timer times out due to inactivity, a critical error is thrown. Another example of a critical error is the IVUS workflow component 222 freezing and being unable to control the manner in which the IVUS acquisition component 220 energizes the IVUS sensor within the patient. Again, a watchdog timer may detect inactivity in IVUS workflow component 222 and throw a critical error. In one embodiment, the resource arbiter component 208 listens for critical errors so that it may take mitigating actions within the token-based synchronization framework.

Referring back to FIG. 5, if a critical error adversely affecting patient safety is detected in decision block 406, the token held by the modality component performing the action is immediately revoked in block 408. As a result, performance of the action is immediately halted to prevent patient harm, as shown in block 410. In one embodiment, token revocation is carried out by dynamically decreasing the number of tokens available to the modality components to zero. As shown in FIG. 6, if the UI framework service 240 throws a critical error, the system controller 202 detects the error and sends a command to all modality extension controllers—such as IVUS extension controller 412—to revoke tokens that authorize actions requiring the user interface. Here, the IVUS extension controller 412 revokes the token from the IVUS acquisition component 220 and IVUS data acquisition immediately halts. As a result, the practitioner performing the IVUS data capture is prevented from harming the patient. If, instead, the IVUS workflow component 222 throws a critical error, the IVUS extension controller 412 detects the error and immediately revokes the acquisition token from the IVUS acquisition component 220. In certain embodiments, the token revocation commands issued by the various components are implemented as function calls to the synchronization library of the resource arbiter component 208. In alternative embodiments, the resource arbiter component 208 may directly perform the token revocation tasks when it detects critical errors.

If in decision block 406 no critical errors are detected during performance of the action, the method continues to blocks 414 and 416 where the modality component continues performing the action and relinquishes the token in a normal manner upon completion of the action.

It is understood that the method 400 for error management within a medical processing system is simply an example embodiment, and in alternative embodiments, additional and/or different steps may be included in the method. For example, in one embodiment, the action authorized by the possession of the token may be a different action than acquiring IVUS data within a patient. For example, the action may be any action that impacts patient safety in some manner, such as applying therapeutic treatments to a sensitive area of patient that may be harmful if not performed precisely. Further, the specific components in the processing system 101 that handle error detection and token revocation tasks may be different than those described in association with the example of FIG. 6. Additionally, the concept of token revocation in response to critical errors is scalable to the processing system-level. When a core platform failure is detected (e.g., a kernel-level failure), a token revocation command may be promulgated throughout the entire system to revoke operational tokens held by all modality components.

Figure 7:
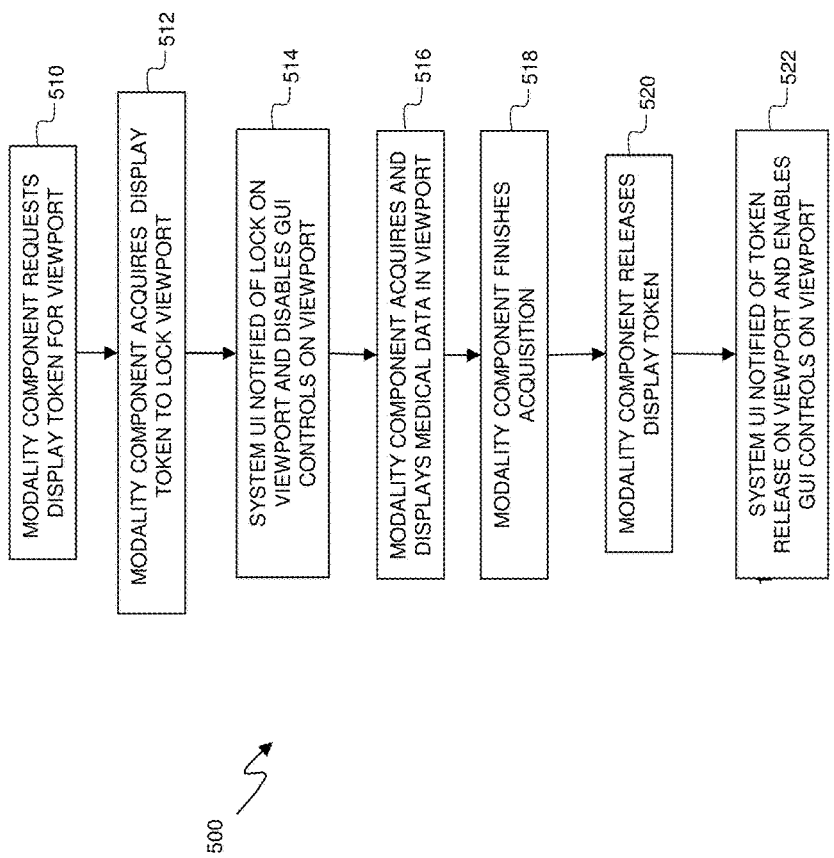
FIG. 7 is a high-level flowchart illustrating a method for display management in a medical processing system according to aspects of the present disclosure.

Referring now to FIG. 7, illustrated is a high-level flowchart illustrating a method 500 for display management in a medical processing system according to aspects of the present disclosure. In particular, the method 500 operates within the token-based framework described in association with FIGS. 3 and 4. During medical sensing procedures performed on a patient, it is common for patient image data to be displayed on a screen as it is being acquired from a patient. The display of data in real-time permits the practitioner to accurately guide the imaging sensor through the patient, for example, during a catheter pull-back procedure. Accordingly, for patient safety reasons, during image acquisition, no other user interface object should obscure the display of patient images. However, user interfaces typically include user-selectable items associated with system-level functionality that are displayed on every user interface screen—for instance, in a common menu bar. Further, in some multi-modality workflows, external patient data, such as x-ray angiography (XA) data, may be used in conjunction with and even co-registered with real-time acquisition data being displayed in a viewport. The token-based system described below ensures, for example, that XA data does not obscure real-time acquisition data, so that medical instruments within a patient may be safely maneuvered by a practitioner.

Figure 8:
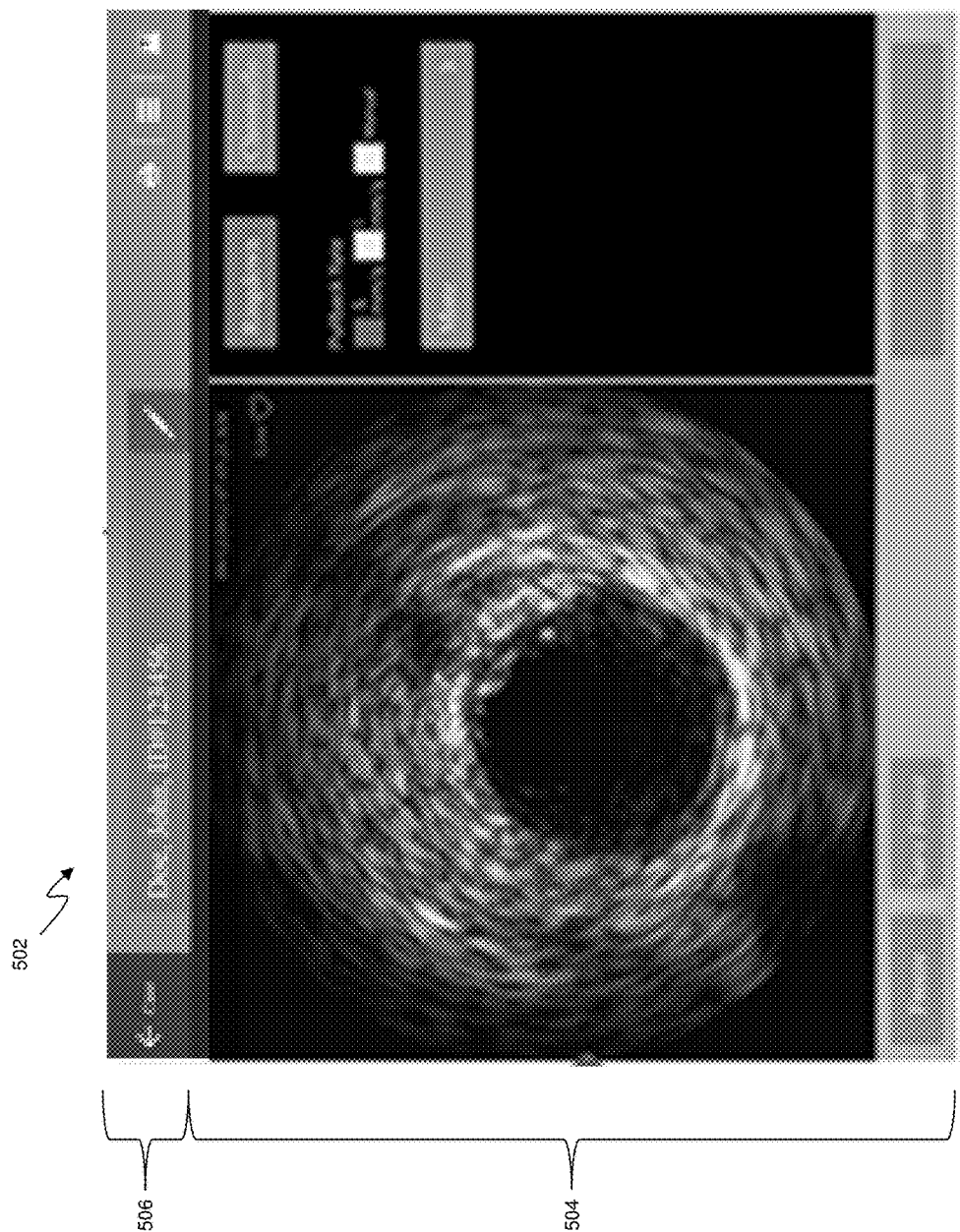
FIG. 8 illustrates an example graphical user interface (GUI) viewport that includes a real-time image acquisition pane and a system tools pane.

In this regard, FIG. 8 illustrates an example graphical user interface (GUI) viewport 502 that includes a real-time image acquisition pane 504 and a system tools pane 506. The acquisition pane 504 displays image data being currently being collected from a patient during a sensing workflow. The system tools pane 506 includes one or more user-selectable buttons such as a menu button and a help button that provide system functionality that is tangential to the acquisition workflow controlled in the acquisition pane 504. Selecting the buttons in the system tools pane 506 may bring up dialogue boxes with further information or options that overlay a portion of or the entire acquisition pane 504. In the illustrated embodiment, the viewport 502 is a touch-screen user interface, and the buttons in the system tools pane 506 are selectable via human touch. In other embodiments, the functionality controlled by the system buttons may be accessed via hardware buttons. The method 500 manages the GUI resources such as the GUI viewport 502 so that real-time patient image data is not obscured and patient safety is not adversely affected.

Figure 9:
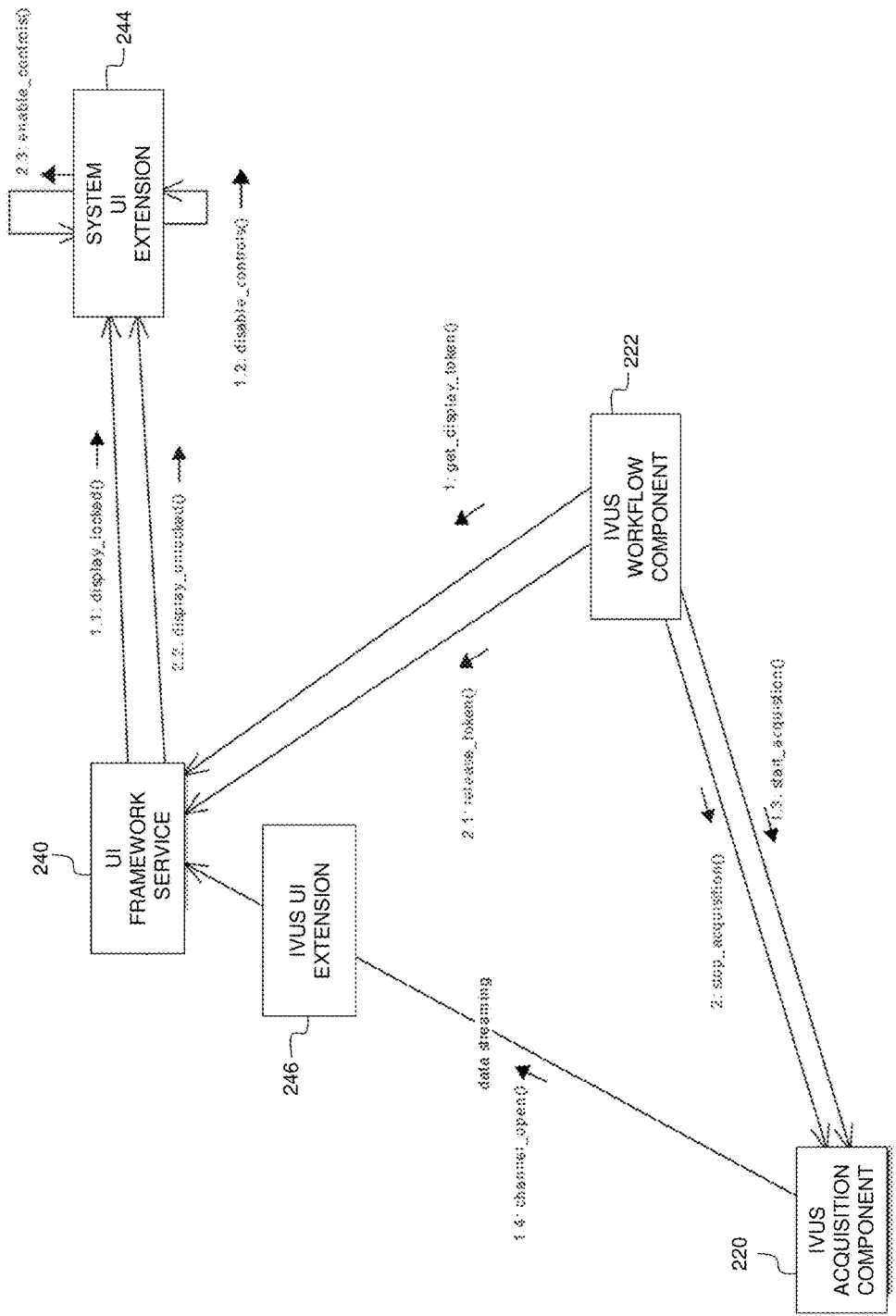
FIG. 9 is a simplified block diagram of a portion of an example IVUS imaging workflow in which an IVUS imaging instrument is capturing image data from within a patient and the image data is being displayed to a practitioner in real-time in a GUI viewport.

In the illustrated embodiment, at least a portion of the method 500 is carried out by various components of the processing framework 200 of FIG. 2. Further, in one embodiment, portions of the method 500 may be implemented as computer-readable instructions stored on a mass storage device or system memory and executed by a processor of the multi-modality processing system 101 of FIG. 1. Further, the method 500 in FIG. 7 is a high-level overview and details associated with various blocks in the method will be described in association with subsequent figures in the present disclosure. In this regard, FIG. 9 is a simplified block diagram of a portion of an example IVUS imaging workflow in which an IVUS imaging instrument is capturing image data from within a patient and the image data is being displayed to a practitioner in real-time in a GUI viewport, such as GUI viewport 502. The system UI extension 244 shown in FIG. 9 is responsible for rendering and accepting user input through the system tools pane 506 in the GUI viewport 502.

Referring back to FIG. 7, the method 500 begins at block 510 where a modality component requests an acquisition display token for a GUI viewport. In the example workflow of FIG. 9, the IVUS workflow component 222 requests an acquisition display token from the UI framework service 240. In certain embodiments, the UI framework service 240 may hold multiple types of tokens corresponding to different display workflows—for example, acquisition display tokens corresponding to real-time display of patient image data as its being acquired and playback tokens corresponding to display of previously-collected image data. Because an acquisition display token is associated with a display action that could have an adverse impact on patient safety if the viewport is obscured, possession of the acquisition display token by one modality component locks access to the viewport by other components including system user interface components. However, possession of the playback token may not lock access to the viewport by other modalities. Thus, in one embodiment, the UI framework service (or other component) may hold only one acquisition display token, but hold a plurality of playback tokens. In other embodiments, such as the one illustrated in FIG. 9, when a modality component takes possession of the acquisition display token, locking signals are transmitted to other modality and system components that have the ability to display information on the viewport for which the token is associated.

In method 500, after an acquisition display token is requested in block 510, the token is passed to the modality component and a lock is established on the viewport in block 512. Next, the method proceeds to block 514 where the other modality and system components that have access to the viewport are notified of the lock. For example, in the illustrated workflow of FIG. 9, when the IVUS workflow component 222 takes possession of the acquisition display token for the GUI viewport 502, the system UI extension 244 is notified of the lock and takes appropriate action. In particular, after the system UI extension receives notification of the lock, it may still render the system tools pane 506, but it will not accept any user input such as the selection of button in the systems tool pane. In other words, the system tools pane buttons become temporality unselectable and do not respond to touches. Further, in certain embodiments, the acquisition pane 504 may also include user-selectable buttons—such as buttons to control the image acquisition—that are rendered and monitored by the IVUS UI extension 246. These buttons would remain user-selectable during the workflow because they are under the control of the modality component in possession of the acquisition display token.

After a lock has successfully been established on the viewport in block 514, the method 500 proceeds to blocks 516 and 518 where the modality component acquires and displays patient data in the view port until acquisition workflow is completed. Because of the locking system described above, any button selections or other user input—accidental or otherwise—to the viewport will not be recognized unless they are directly related to the acquisition workflow. In this manner, real-time patient data displayed in the acquisition pane 504 will not be obscured during image acquisition and patient safety will not be adversely affected.

Next, the method 500 proceeds to block 520 where the modality component releases the acquisition display token. Finally, in block 522, upon release of the acquisition token, the other modality and system components that have access to the viewport are notified of the lock release on the viewport. As a result, the temporarily locked buttons are restored to a user-selectable state. For example, in the illustrated workflow of FIG. 9, when the IVUS workflow component 222 releases the acquisition display token for the GUI viewport 502, the system UI extension 244 is notified and re-activates the buttons in the system tools pane 506. The acquisition display token may now be requested by another modality component.

It is understood that the method 500 for display management in a medical processing system is simply an example embodiment, and in alternative embodiments, additional and/or different steps may be included in the method. For example, in certain embodiments, a procedure other than data acquisition display may trigger the lock on the viewport. For instance, a therapeutic procedure may require a practitioner to follow precise instructions on a viewport, and any interruption could be harmful to the patient. Accordingly, the method 500 is applicable to any patient procedure that requires, for patient safety reasons, information displayed in viewport to be viewable during the entirety of the procedure, without interruption. Additionally, the resource arbiter component 208 may be responsible for detecting the acquisition of a display token and notifying the system UI extension of the lock so that it disables the buttons in the system tools pane 506.

Although illustrative embodiments have been shown and described, a wide range of modification, change, and substitution is contemplated in the foregoing disclosure and in some instances, some features of the present disclosure may be employed without a corresponding use of the other features. Further, as described above, the components and extensions described above in association with the multi-modality processing system may be implemented in hardware, software, or a combination of both. And the processing systems may be designed to work on any specific architecture. For example, the systems may be executed on a single computer, local area networks, client-server networks, wide area networks, internets, hand-held and other portable and wireless devices and networks. It is understood that such variations may be made in the foregoing without departing from the scope of the present disclosure. Accordingly, it is appropriate that the appended claims be construed broadly and in a manner consistent with the scope of the present disclosure.

What is claimed is:

1. A method of resource management in a multi-modality medical device, comprising:
   initializing a case associated with a patient undergoing a multi-modality medical procedure that includes a workflow action to be performed by each of a plurality of modality components within the multi-modality medical device, the multi-modality medical device further comprising a case management component and a resource arbiter component each in communication with the plurality of modality components, wherein the multi-modality medical device comprises a single device including the plurality of modality components, the case management component, and the resource arbiter component such that the case management component and the resource arbiter component are each in communication with the plurality of modality components within the single device;
   determining if the patient is permitted to undergo the multi-modality medical procedure;
   in response to determining the patient is permitted to undergo the multi-modality medical procedure, making a token available to the plurality of modality components by the case management component, the token being representative of authorization for at least one modality component to perform the workflow action for the multi-modality medical procedure;
   receiving, at the case management component via the resource arbiter component, a first request for the token from a first modality component associated with a first medical modality, wherein the first modality component controls operation of an intravascular guidewire or catheter to acquire intravascular data associated with a vessel of the patient, the intravascular guidewire or catheter comprising a flexible elongate member sized and shaped for positioning within the vessel of the patient, the intravascular guidewire or catheter further comprising a sensor configured to obtain the intravascular data;
   passing the token from the case management component to the first modality component, possession of the token by the first modality component indicating that the first modality component is at least one of an authorized modality component to perform the workflow action for the multi-modality medical procedure, wherein the workflow action comprises acquiring the intravascular data by the intravascular guidewire or catheter;
   receiving, at the case management component, the token from the first modality component;
   receiving, at the case management component via the resource arbiter component, a second request for the token from a second modality component associated with a second medical modality different from the first medical modality; and
   passing the token from the case management component to the second modality component, possession of the token by the second modality component indicating that the second modality component is at least one of an authorized modality component to perform the workflow action for the multi-modality medical procedure.

2. The method of claim 1, further including:
   subsequent to receiving the second request and prior to passing the token to the second component, determining whether the token is available; and
   if the token is not available, waiting for the token to become available before performing the passing the token to the second component.

3. The method of claim 1, further including, subsequent to passing token to the first component and prior to receiving the token from the first component, preventing the second component from performing the workflow action.

4. The method of claim 1, wherein the action includes displaying medical data associated with the patient on a display resource within the multi-modality medical device.

5. The method of claim 1, wherein the workflow action includes applying a therapy to a patient.

6. The method of claim 1, further including, revoking the token from the first modality in response to detecting an error that adversely affects patient safety.

7. The method of claim 1, further including:
closing the case; and
in response to closing the case, making the token unavailable to the plurality of modality components.

8. The method of claim 1, wherein the first medical modality and second medical modality are respectively associated with one of intravascular ultrasound (IVUS) imaging, intravascular photoacoustic (IVPA) imaging, optical coherence tomography (OCT), forward looking IVUS (FL-IVUS), fractional flow reserve (FFR), x-ray angiography (XA), or coronary flow reserve (CFR).

9. The method of claim 1, wherein the workflow action comprises at least one of a diagnostic or a therapeutic medical procedure associated with a vessel of the patient.

10. A method of error management in a multi-modality medical device, comprising:
initializing a case associated with a patient undergoing a multi-modality medical procedure that includes a workflow action to be performed by a modality component within the multi-modality medical device;
determining if the patient is permitted to undergo the multi-modality medical procedure;
receiving, from the modality component, a request for a token representative of authorization to perform the workflow action;
in response to determining the patient is permitted to undergo the multi-modality medical procedure, passing the token to the modality component in the multi-modality medical device, possession of the token by the modality component indicating that the modality component is authorized to perform the workflow action associated with the patient for the multi-modality medical procedure, wherein the multi-modality medical device further comprises a system controller, a modality extension controller, and a modality workflow component, wherein the multi-modality medical device comprises a single device including the modality component, the system controller, the modality extension controller, and the modality workflow component;
performing, by the modality component, the workflow action on the patient, wherein the workflow action comprises acquiring intravascular data associated with a vessel of the patient by an intravascular guidewire or catheter comprising a flexible elongate member sized and shaped for positioning within the vessel of the patient, the intravascular guidewire or catheter further comprising a sensor configured to obtain the intravascular data, wherein the modality component controls operation of the intravascular guidewire or catheter;
detecting, while the modality component is performing the workflow action, an error that adversely affects the safety of the patient; and
in response to detecting error, revoking, by the modality extension controller in communication with the system controller and the modality workflow component, the token from the modality component to stop the performance of the workflow action.

11. The method of claim 10, wherein the error inhibits acquiring the medical data.

12. The method of claim 10, wherein acquiring the medical data includes displaying images associated with the medical data on a display.

13. The method of claim 12, wherein the error inhibits displaying the images on the display.

14. The method of claim 10, wherein the medical data is associated with one of intravascular ultrasound (IVUS) imaging, intravascular photoacoustic (IVPA) imaging, optical coherence tomography (OCT), forward looking IVUS (FL-IVUS), fractional flow reserve (FFR), x-ray angiography (XA), or coronary flow reserve (CFR).

15. The method of claim 10, wherein workflow action includes applying a treatment to the patient.

16. The method of claim 10, wherein revoking the token includes reducing the number of tokens available to the modality component to zero.

17. The method of claim 10,
wherein the token is one of a plurality of tokens possessed by a plurality of modality components; and
wherein the revoking includes revoking each of the plurality of tokens from a respective one of the plurality of modality components.

18. The method of claim 10, wherein detecting the error includes monitoring for a lack of activity by a component the modality component depends upon.

19. A system, comprising:
an intravascular guidewire or catheter comprising a flexible elongate member sized and shaped to be positioned within a vessel of a patient, the intravascular guidewire or catheter further comprising a sensor configured to obtain intravascular data associated with the vessel of the patient; and
a multi-modality medical device in communication with the intravascular guidewire or catheter, wherein the multi-modality medical device is a single device comprising:
a first modality component associated with a first modality and operable to perform a workflow action in a multi-modality medical procedure, the workflow action including receiving the intravascular data obtained by the intravascular guidewire or catheter while positioned within the vessel of the patient;
a case management component operable to make a token available to a plurality of modality components respectively associated with a plurality of modalities of the multi-modality medical procedure following initialization of a case associated with the patient undergoing the multi-modality medical procedure and a determination that the patient is permitted to undergo the multi-modality medical procedure, wherein the first modality component is one of the plurality of modality components and the first modality is one of the plurality of modalities, the token being representative of authorization for the modality component to perform the workflow action; and
a resource arbiter component in communication with the plurality of modality components and operable to receive a request for the token from the first modality component,
wherein the case management component is further operable to pass the token to the first modality component in response to the request received by resource arbiter component and to receive the token from the first modality component when the workflow action is complete.

* * * * *